(12) United States Patent
Lipford et al.

(10) Patent No.: US 11,896,521 B2
(45) Date of Patent: Feb. 13, 2024

(54) DEVICES, METHODS AND USES FOR REMOVING HEAT, ENERGY AND FLUIDS FROM A MAMMAL

(71) Applicant: CoolTech, LLC, Baltimore, MD (US)

(72) Inventors: Brian Lipford, Baltimore, MD (US); Tandri Harikrishna, Ellicott City, MD (US); Ben Lane, Hydes, MD (US); Aaron Pearl, Baltimore, MD (US)

(73) Assignee: CoolTech, LLC, Baltimore, MD (US)

( * ) Notice: Subject to any disclaimer, the term of this patent is extended or adjusted under 35 U.S.C. 154(b) by 139 days.

(21) Appl. No.: 16/927,647

(22) Filed: Jul. 13, 2020

(65) Prior Publication Data

US 2021/0128347 A1 May 6, 2021

Related U.S. Application Data

(63) Continuation of application No. 14/578,094, filed on Dec. 19, 2014, now abandoned.

(60) Provisional application No. 62/090,816, filed on Dec. 11, 2014, provisional application No. 62/089,370, filed on Dec. 9, 2014, provisional application No. 62/052,187, filed on Sep. 18, 2014, provisional application No. 61/970,034, filed on Mar. 25, 2014, provisional application No. 61/948,248, filed on Mar. 5, 2014, provisional application No. 61/935,521, filed on Feb. 4, 2014, provisional application No. 61/918,259, filed on Dec. 19, 2013.

(51) Int. Cl.
*A61F 7/12* (2006.01)
*A61K 33/00* (2006.01)
*A61K 45/06* (2006.01)
*A61B 18/00* (2006.01)
*A61B 18/14* (2006.01)
*A61F 7/00* (2006.01)

(52) U.S. Cl.
CPC ............... *A61F 7/12* (2013.01); *A61K 33/00* (2013.01); *A61K 45/06* (2013.01); *A61B 18/1492* (2013.01); *A61B 2018/00017* (2013.01); *A61B 2018/00351* (2013.01); *A61B 2018/00488* (2013.01); *A61B 2018/00577* (2013.01); *A61F 2007/0006* (2013.01); *A61F 2007/006* (2013.01); *A61F 2007/0068* (2013.01)

(58) Field of Classification Search
CPC ... A61B 2018/00017; A61F 2007/0068; A61F 7/12
See application file for complete search history.

(56) References Cited

U.S. PATENT DOCUMENTS

2013/0204331 A1 * 8/2013 Harikrishna .......... A61F 7/0085
607/107

* cited by examiner

*Primary Examiner* — Deanna K Hall
(74) *Attorney, Agent, or Firm* — Whiteford, Taylor & Preston, LLP; Peter J. Davis

(57) ABSTRACT

The present invention provides improved devices for removing energy and fluid from body fluid containing spaces and surfaces of a mammal, and new uses for such devices, including fluid removal, energy removal, increasing metabolic rate; promoting weight loss; preventing esophageal burn-through, reducing beta-amylase accumulation in the brain, delaying or inhibiting the onset of Alzheimer's and other senile dementia.

3 Claims, 13 Drawing Sheets

DEVICES, METHODS AND USES FOR REMOVING HEAT, ENERGY AND FLUIDS FROM A MAMMAL

This application is based upon and claims priority from U.S. Provisional Patent Application Ser. No. 61/918,259 entitled "COOLSTAT: TRANSNASAL COOLING FOR PRE-HOSPITAL CARDIAC ARREST," filed with the United States Patent and Trademark Office on Dec. 19, 2013 by the inventors herein, and from U.S. Provisional Patent Application Ser. No. 61/935,521 entitled "METHOD AND DEVICE FOR NON-INVASIVE ANATOMICAL AND SYSTEMIC COOLING AND NEUROPROTECTION," filed with the United States Patent and Trademark Office on Feb. 4, 2014 by the inventors herein, and from U.S. Provisional Patent Application Ser. No. 61/948,248 entitled "METHOD AND DEVICE FOR NON-INVASIVE ANATOMICAL AND SYSTEMIC COOLING AND NEUROPROTECTION, AND FOR REDUCTION OF BETA-AMYLOID ACCUMULATION IN THE BRAIN," filed with the United States Patent and Trademark Office on Mar. 5, 2014 by the inventors herein, and from U.S. Provisional Patent Application Ser. No. 61/970,034 entitled "METHOD AND DEVICE FOR NON-INVASIVE ANATOMICAL AND SYSTEMIC COOLING AND NEUROPROTECTION, INCLUDING VASODILATION," filed with the United States Patent and Trademark Office on Mar. 25, 2014 by the inventors herein, and from U.S. Provisional Patent Application Ser. No. 62/052,187 entitled "PULSED AIR DELIVERY TO NASAL TURBINATES FOR NEUROCOOLING AND ENERGY REMOVAL," filed with the United States Patent and Trademark Office on Sep. 18, 2014 by the inventors herein, and from U.S. Provisional Patent Application Ser. No. 62/089,370 entitled "METHOD AND DEVICE FOR NON-INVASIVE ANATOMICAL AND SYSTEMIC COOLING AND NEUROPROTECTION, INCLUDING TWO-SIDED HEAT SINK," filed with the United States Patent and Trademark Office on Dec. 9, 2014 by the inventors herein, and from U.S. Provisional Patent Application Ser. No. 62/090,816 entitled "METHOD AND DEVICE FOR NON-INVASIVE ANATOMICAL AND SYSTEMIC COOLING AND NEUROPROTECTION, INCLUDING TWO-SIDED HEAT SINK," filed with the United States Patent and Trademark Office on Dec. 11, 2014 by the inventors herein, the specifications of which are incorporated herein by reference in their entireties.

BACKGROUND OF THE INVENTION

1. Field of the Invention

The invention relates generally to methods and devices for removing heat, energy, and/or fluid from a living mammal

2. Background Information

Methods and devices for non-invasive anatomical and systemic cooling and neuroprotection are disclosed in PCT/US2011/025121 and U.S. patent application Ser. No. 13/579,370.

SUMMARY OF THE INVENTION

The present inventions include improvements to and new uses for the methods and devices disclosed in PCT/US2011/025121, and U.S. patent application Ser. No. 13/579,370, the disclosures of which are incorporated herein in their entirety. These improvements include additive cooling effect by simultaneous passage of dry gas across the mucous membranes of two or more anatomical features; chemically stimulating the mucous membranes to increase water production to prevent over-drying and increase cooling; providing an external source of water to the mucous membranes for the same purpose; providing a source of negative pressure to draw the gas across the mucous membranes (instead of or in addition to pushing it) to promote vasodilation and improve the evaporative model; pulsing and/cycling the gas across the mucous membranes, and in particular the nasal turbinates to reduce discomfort; and the addition of one, two, or more heat exchangers in the device to remove heat from the air caused by the desiccant.

The present invention also includes new uses for the devices and methods disclosed in PCT/US2011/025121 and U.S. patent application Ser. No. 13/579,370, including fluid extraction from a mammal, especially in cases of refractory heart failure and other conditions in which the body retains excess fluid, energy extraction from a mammal, increasing the metabolic rate in a mammal, promoting weight loss in a mammal, prevention of esophageal burn-through during catheter ablation treatment for atrial fibrillation, reduction or inhibition of β-amyloid accumulation in a mammal, and/or delay in onset or amelioration of senile dementia and/or Alzheimer's in a human, by utilizing the nasal heat loss mechanism wherein heat and fluid is shed by the body due to its natural response to humidify and condition the inspired air.

Evaporative cooling is a physical phenomenon in which the evaporation of a liquid results in the cooling of an object or a liquid in contact with it, due to the fact that it requires heat or energy to change a liquid into a gas. The amount of energy required to change a liquid to a gas is directly proportional to the total mass of liquid that is changed to a gas and the enthalpy of vaporization. Enthalpy of vaporization, also referred to as latent heat of vaporization, is the amount of energy required to transform a given quantity of a substance from a liquid into a gas. Different liquids have different enthalpies of vaporization.

The present invention makes use of this phenomenon to achieve energy and fluid removal from the human body. According to the invention, dry air is blown across one or more mucus membranes, which promotes the liquid water (coming from the mucus membranes) to evaporate. The heat or energy needed to vaporize the water is extracted from the host surface and transported out of the body.

The dry air may be provided to the patient via a standard nasal mask, a nasal pillow or other standard device used to deliver gasses to a patient. According to a preferred embodiment, air is fed to the patient through the nose and is allowed to exit the mouth. According to one embodiment, a bite-block or other device may be used to keep the mouth open in order to allow the air introduced through the nose to exit through the mouth.

According to various aspects of the invention, therefore, there is provided a method of for removing heat and/or other energy from a mammal; cooling an anatomical feature in a mammal, providing systemic cooling in a mammal, removing excess fluid from a mammal, raising the metabolic rate of a mammal, promoting weight loss in a mammal, prevention of esophageal burn-through during catheter ablation treatment for atrial fibrillation, reduction or inhibition of β-amyloid accumulation in a mammal, and/or delay in onset or amelioration of senile dementia and/or Alzheimer's in a human, by controlled, induced evaporation of a bodily fluid from a bodily fluid-containing space or surface, such as a mucus containing-space or surface in the mammal The method includes delivering a dry gas (compressed or not) which does not include a coolant (i.e., a refrigerant or chilled gas or vapor) into or upon the bodily fluid-containing space or surface to provide controlled evaporation and transport (removal) of the bodily fluid upon contact with the dry gas. Such evaporation and transport of the bodily fluid produces removes heat, energy and fluid from the body.

Accordingly, the present invention further provides an improved device for removing heat and/or other energy from a mammal; cooling an anatomical feature in a mammal, providing systemic cooling in a mammal, removing excess fluid from a mammal, raising the metabolic rate of a mammal, promoting weight loss in a mammal, prevention of esophageal burn-through during catheter ablation treatment for atrial fibrillation, reduction or inhibition of β-amyloid accumulation in a mammal, and/or delay in onset or amelioration of senile dementia and/or Alzheimer's in a human, by evaporation of a fluid from a bodily fluid-containing space or surface in the mammal. The device may include: a) a conduit which includes a proximal end, a distal end, a first lumen extending between the proximal and distal ends, and one or more fluid delivery ports at the distal end in fluid communication with the first lumen; and b) a fluid source in fluid communication with the proximal end of the first lumen for supplying a dry fluid not containing a coolant to the first lumen; wherein the device is configured such that fluid flows distally along the first lumen through the fluid delivery ports to contact the bodily fluid- containing space or surface upon expansion of the fluid through the fluid delivery ports. If the dry fluid is compressed, a compressor may be provided to the fluid source; or the fluid may be provided in pre-compressed condition; e.g., in a valved tank or other canister.

In various embodiments, the device further includes: c) a second lumen extending toward the distal end of the conduit; d) one or more return ports at the distal end in fluid communication with the second lumen; and e) an exhaust port in fluid communication with the proximal end of the second lumen; wherein the device is configured such that fluid flows distally along the first lumen through the fluid delivery ports and reenters the second lumen through the return ports.

In some embodiments, the device also further includes one or more temperature sensors (for the fluid and/or the treated mammal), pressure sensor and/or fluid flow regulator. In some embodiments the device includes a third lumen extending toward the distal end of the conduit, and one or more additional gas delivery ports at the distal end in communication with the third lumen and/or the exhaust ports. The device may be configured to be lightweight and portable, and may be configured to operate via connection to standard wall socket and/or optionally by onboard rechargeable battery. The device may optionally include a disposable desiccant cartridge and may be provided with optional inputs for receiving air and/or other gases via an external tank. The invention is particularly well-suited to use in ambulatory therapies, including emergency settings, combat settings, sport settings, and even clinic and home-use settings.

BRIEF DESCRIPTION OF THE DRAWINGS

Various features and advantages of the disclosure will become more apparent by the following detailed description of several embodiments thereof with reference to the attached drawings, of which.

DETAILED DESCRIPTION OF THE INVENTION

Figure 1:
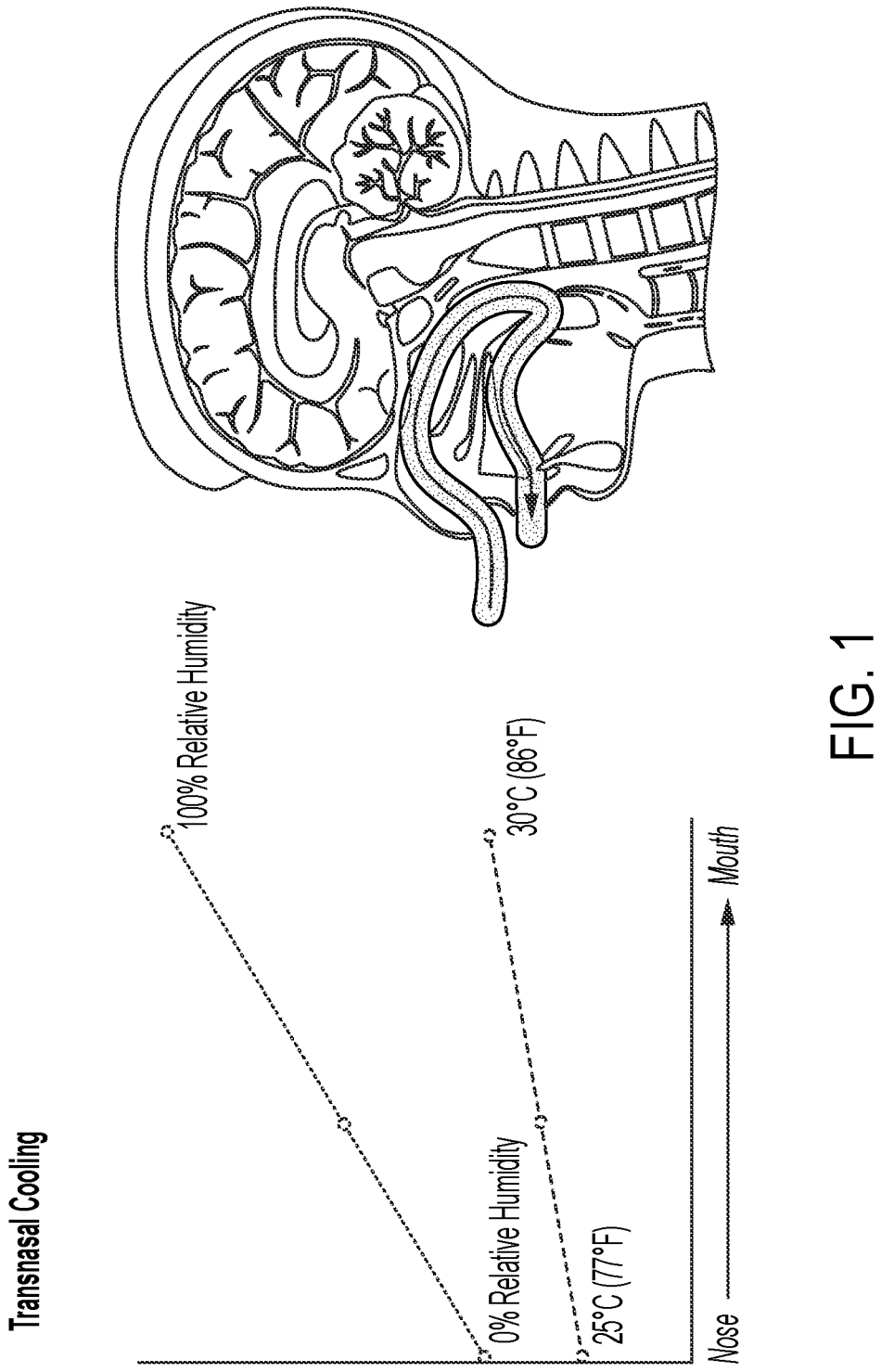
FIG. 1 is a representation of Transnasal cooling according to an embodiment of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, "absolute humidity" is used to refer to the amount of water vapor in a gaseous mixture of gas and water vapor as expressed by mass. "Relative humidity" is used to refer to the amount of water vapor that exists in a gaseous mixture of gas and water vapor as a function of its current state, for example temperature. Essentially, relative humidity is a measure of the amount of moisture in the air compared to what the air is capable of holding at a given temperature. In various embodiments, the relative humidity of the gas before being contacted with a bodily fluid is less than or equal to about 90, 80, 70, 60, 50, 40, 30, 20, 10, 5 or 0%. In various embodiments, the relative humidity of the gas after being contacted with a bodily fluid is greater than or equal to about 0, 10, 20, 30, 40, 50, 60, 70, 80 or 90%.

As used herein, a "dry" fluid or gas is used to refer to a fluid or gas that is unsaturated with water vapor or other liquid vapor. In various embodiments, the dry gas has a relative humidity of less than or equal to about 90, 80, 70, 60, 50, 40, 30, 20, 10, 5 or 0%.

Several types of gases are suitable for use with the present invention. Such gases include, but are not limited to air, $NO_2$, $CO_2$, $O_2$, and inert gases, such as He, Ar, and Xe, as well as combinations thereof. In related embodiments, the gas may be an anesthetic, such as $N_2O$ or Xe, or a gas which additionally may have neuroprotective properties and systemic effects to promote systemic cooling, such as vasodilation.

As used herein in reference to optional embodiments, the term "compressed" gas is used to refer to a gas that is under greater pressure than atmospheric. Compression of a dry gas may optionally be employed to allow for its delivery at low flow rates compared to those required to induce the same evaporative response to a dry gas at atmospheric pressure.

In various embodiments, the pressure of the compressed gas, if employed, is regulated above atmospheric pressure, for example above about 10-15 psi. For example, the gas may be regulated to about 10, 15, 20, 25, 30, 35, 40, 45, 50, 55, 60, 65, 70, 75, 80, 85, 90, 95, 100, 105, 110, 115, 120, 125, 130, 135, 140, 145, 150 cmH2O or greater. To assist in regulating the pressure of the compressed gas, the fluid source may be a compressed gas source. Additionally, the device may further include one or more valves disposed along the conduit to regulate pressure and flow of the gas.

The dry gas delivered according to the invention does not include a coolant (and may be, but need not be, warmed). As used herein, the term "coolant" includes volatile gases and may include dry ice, liquid nitrogen chilled saline, chilled water, anti-freeze solution, refrigerants, such as fluorocarbons, chlorofluorocarbons (CFCs), hydrochlorofluorocarbons (HCFCs), perfluorocarbons (PFCs), R-134a (1,1,1,2 tetrafluoro ethane), Freon™, and other cooling fluids or refrigerants, or a combination thereof. A coolant may also be considered any fluid chilled to a temperature 10° C. or more below normal body temperature. For humans, a coolant would thus be a fluid chilled to about 27, 26, 25, 24, 23, 22, 21, 20, 19, 18, 17, 16, 15, 14, 13, 12, 11, 10, 9, 8, 7, 6, 5, 4, 3, 2, 1, 0° C. or less.

As used herein, the term "warm" refers to a temperature of room temperature or greater. As such warm air may be greater than about 20, 21, 22, 23, 24, 25, 26, 27, 28, 29, 30, 31, 32, 33, 34, 35, 36, 37, 38, 39, 40° C. or greater.

In one embodiment, delivery of cooler gas is envisioned where a lower rate of evaporation is desired, for example when a longer duration of therapy is desired. As such the gas or air may be greater than about 0, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. In preferred embodiments of the invention, however, the dry fluid will be at normal body temperature (e.g., for humans, 37° C.) or warmer to a clinically acceptable temperature, with dry fluid at the ambient environmental temperature being particularly suitable for ambulatory settings, especially in emergency contexts.

The invention may utilize high flow of gas, which includes flow rates of between about 20 and 200 L/min, between about 40 and 130 L/min, between about 20 and 80 L/min, between about 40 and 500 L/min, between about 100 and 500 L/min, or between about 200 and 500 L/min For example, gas may be delivered at a flow rate of greater than about 10, 15, 20, 25, 30, 35, 40, 45, 50, 60, 65, 70, 75, 80, 85, 90, 95, 100, 105, 110, 115, 120, 125, and 130 L/min As discussed herein, the flow rate may be varied throughout the duration of delivery to maximize evaporation within or on the bodily fluid-containing space or surface.

According to metabolic rate increase and weight loss embodiments, the system could be used at a lower dose settings, perhaps overnight or during the day, for extended periods of time, and the flow rate is preferably set at a lower range, for example between about 10 and 40 L/Min, to improve long term tolerability. This would extract a smaller amount of energy from the body, which if done over longer periods, would result in slightly higher metabolic rates and weight loss The term "bodily fluid" as used herein may encompass a variety of different fluid types. Such fluids may include, but are not limited to mucus, saliva, gastric fluid, urine, sweat and the like.

Figure 2:
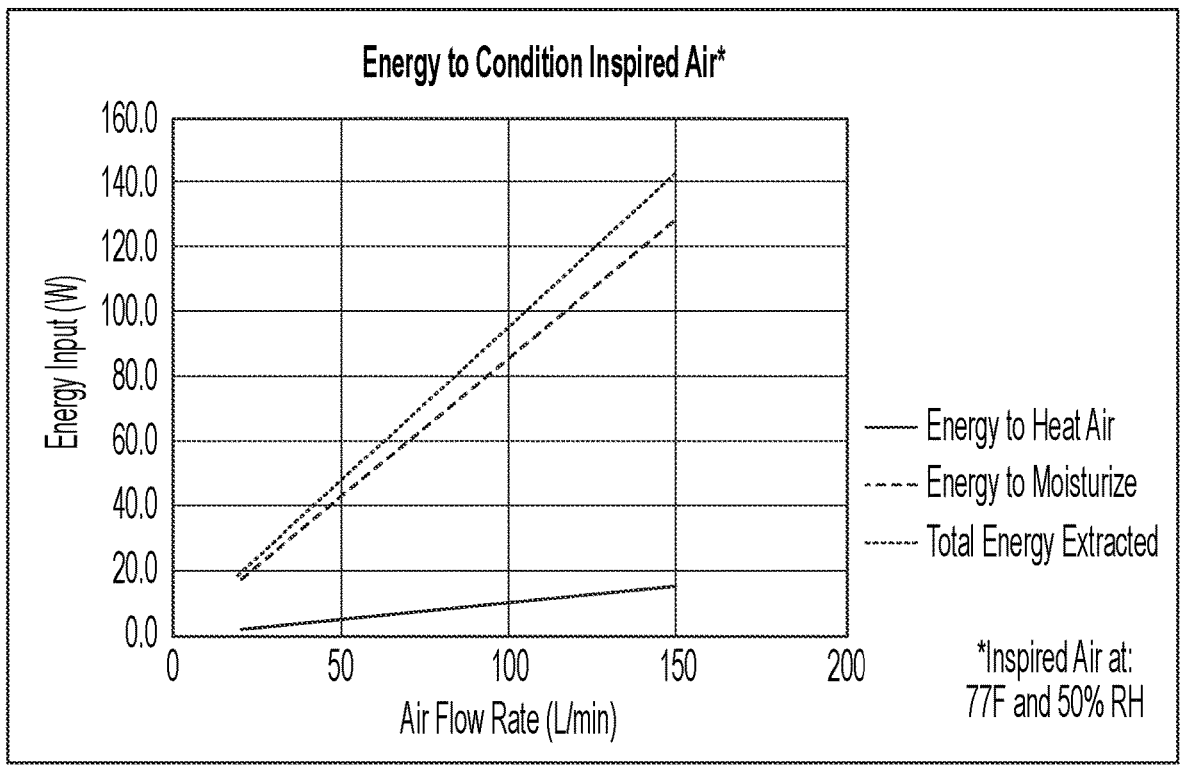
FIG. 2 is a graph showing the energy required by a mammal to condition (heat and moisturize) inspired air to the temperature and humidity appropriate for inhalation to the lungs.

In the normal respiratory process, inspired air is conditioned prior to entering lungs. Air is heated to near body temperature, and is fully humidified. See FIG. 1. During normal expiration (normal respiration air volumes), moisture used to humidify inspired air is recaptured by the nasal turbinates as a means to conserve energy. FIG. 2 shows the energy required by a mammal to condition inspired air to the temperature and humidity appropriate for normal lung function at varying air flow rates. The lower, black, line shows the energy required to heat air inspired at 77° F. to 86° F.; the middle, blue, line shows the energy required to moisturize air inspired at 50% relative humidity to 100% relative humidity.

Figure 3:
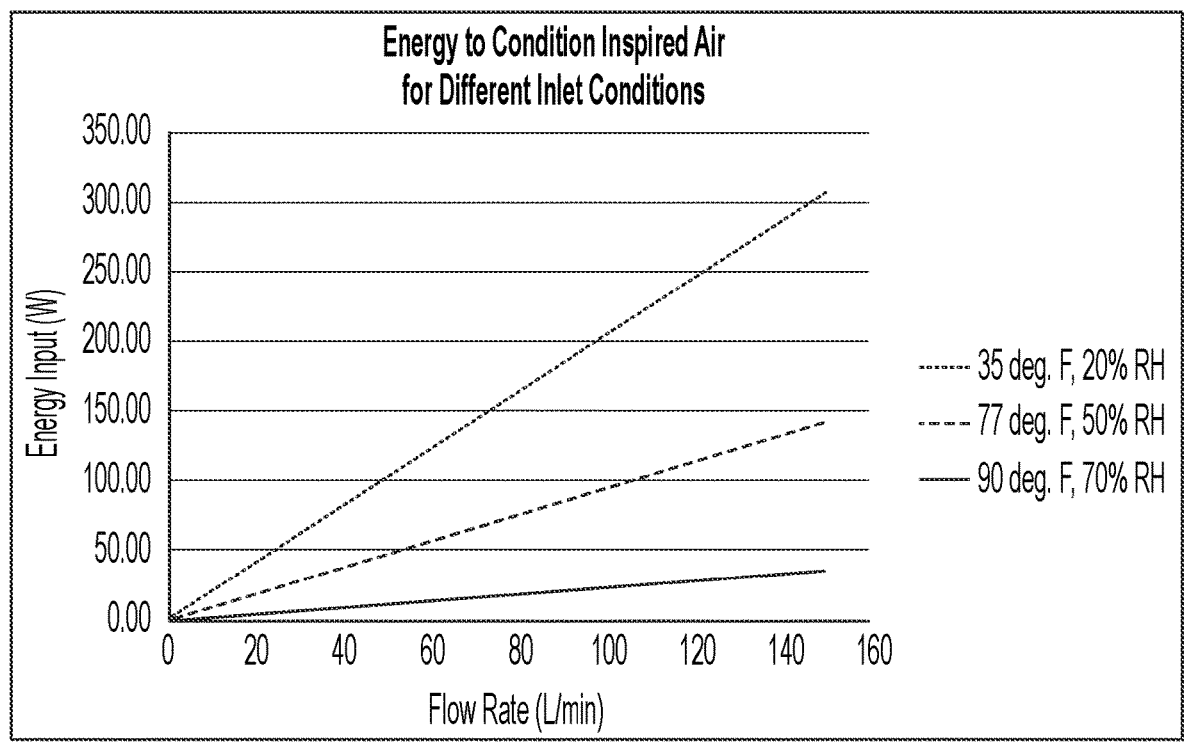
FIG. 3 is a graph showing the energy required by a mammal to condition inspired air at different inlet conditions.

FIG. 3 shows the energy required by a mammal to condition three different inspired air conditions to temperature and humidity appropriate for normal lung function at varying flow rates. The bottom, black, line shows the energy necessary to condition air inspired at 90° F. and 70% relative humidity. The middle, blue, line shows the energy necessary to condition air inspired at 77° F. and 50% relative humidity, and the red line shows the energy necessary to condition air inspired at 35° F. and 20% relative humidity.

Figure 4:
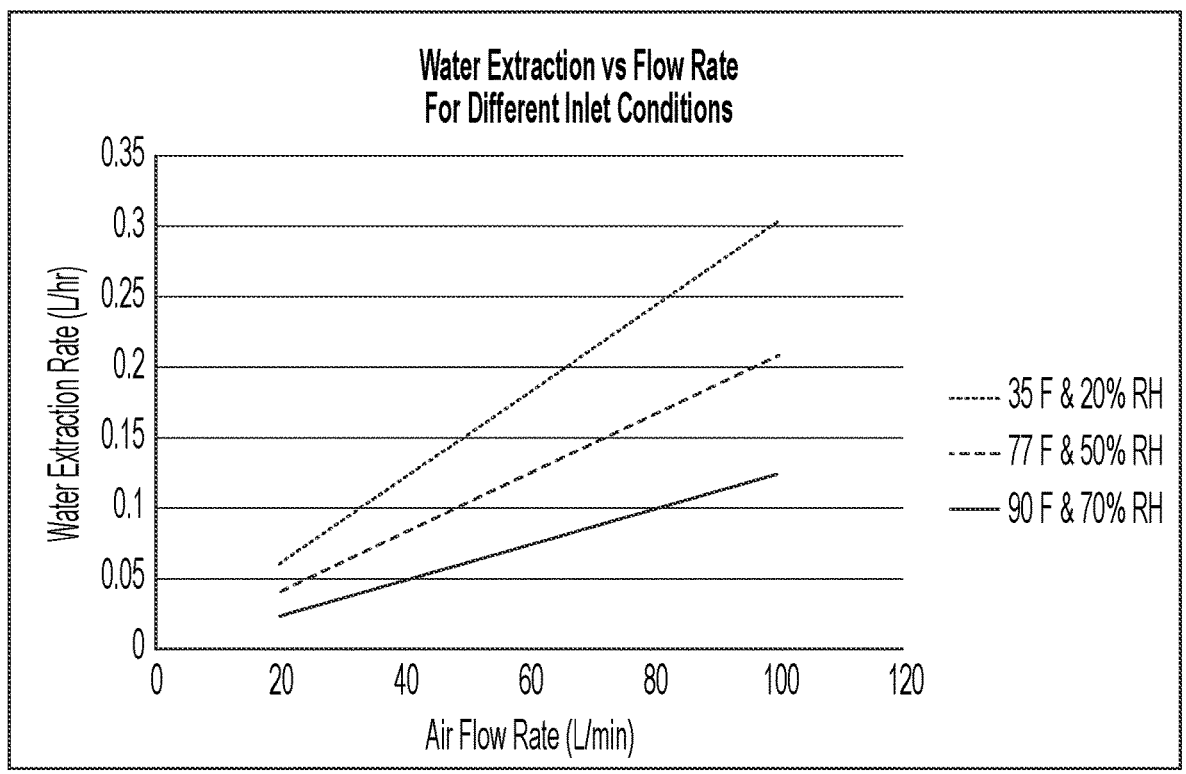
FIG. 4 is a graph showing the water extraction rate according to an embodiment of the present invention versus air flow rate at different inlet conditions.

FIG. 4 shows the water extraction versus flow rate for different inspired air conditions. The bottom, black, line shows the water extraction rate versus air flow rate for air inspired at 90° F. and 70% relative humidity. The middle, blue, line shows the water extraction rate versus air flow rate for air inspired at 77° F. and 50% relative humidity, and the red line shows the water extraction rate versus air flow rate for air inspired at 35° F. and 20% relative humidity.

The heat/energy/fluid removal model according to the invention can also be used in series or parallel with two or more mucus membranes throughout the body. The inventors have discovered that different mucous membranes may be used in an additive fashion to increase the amount of energy removal, cooling, fluid removal, and other effects. In particular, the inventors have observed in animal studies that the simultaneous flow of dry air/gas across the mucous membranes in nasal turbinates and in the esophagus resulted in increased cooling. Accordingly, this invention includes methods and devices which introduce dry non-coolant gas/air to the nasal turbinates and which simultaneously also introduce dry non-coolant gas/air to mucous membranes in the esophagus or other body-fluid containing spaces/tissues.

Accordingly, the invention includes fluid extraction from a mammal, and/or metabolic rate increase, and/or weight loss, prevention of esophageal burn-through during catheter ablation treatment for atrial fibrillation, reduction or inhibition of β-amyloid accumulation in a mammal, and/or delay in onset or amelioration of senile dementia and/or Alzheimer's in a human, by evaporation of a fluid from a bodily fluid-containing space or surface of the mammal. These methods may be carried out using the devices disclosed in PCT/US2011/025121, and U.S. patent application Ser. No. 13/579,370, the disclosures of which are incorporated herein in their entirety, especially including paragraph [0046] and FIG. 2 of U.S. patent application Ser. No. 13/579,370.

According to the energy and heat removal aspects of the invention, the invention provides methods for reducing overheating and providing comforting and/or therapeutic cooling in cases of heat related stress, including overheating resulting from sport and/or combat activities, fever, heat exhaustion and heat stroke.

As the energy removal process described herein may be limited by a number of variables, including the rate of air flow of dry air (that stimulates the evaporative process) and the amount of water that can be supplied by the mucus membranes and mucosal integrity when exposed to dry air. Over time, removal of water from a mucosal tissue might inhibit its ability to secrete mucus, potentially limiting the amount of additional evaporative cooling, regardless of the amount of dry air flow supplied to that region.

Accordingly, the present invention presents methods to chemically stimulate the mucus membranes to increase production of water and/or to provide an external source of water to prevent desiccation of the mucosa and/to maintain the health and integrity of the mucosa. External sources of water might include an atomizer or nebulizer to continuously or intermittently spray water into or on a region of interest internal to the body. Chemically stimulation of mucus production may be achieved using expectorants such as hypertonic saline, cholinergic agents and guaifenesin. Increasing the amount of water available for evaporative cooling will increase the cooling rate and/or the time period over which the cooling operation can be performed. Another advantage of this aspect of the invention is that it can be designed to be 'water neutral', i.e., it can be designed such that there is no net water extracted from the human Additionally, intermittent hydration of the mucosa can reduce chances of infection due to breach of mucosal defenses.

The invention also provides a method for removing excess body fluids in cases where removal of fluids is useful in the treatment of certain conditions including refractory heart failure, in which the body retains fluid in extremities. In conditions of cardiac stress, a patient will build up excess water in the extremities. Presently, the primary way to remove water from the body is via urination by the use of diuretic drugs. This method can take a significant period of time, and may not be useful especially in patients with compromised renal conditions. Accordingly, the present invention represents a significant advance in the treatment of such conditions.

During traumatic brain injury (TBI), primary injury results from displacement of the brain and related structures during the initial trauma; however, the most significant effects of TBI are often the result of progressive and complex processes of secondary brain injury (SBI) which take place well after the initial trauma (Scalea et al., 1994). Expression and abnormal release of various cellular factors during SBI can damage brain cells, cause dysfunction of the blood-brain barrier, aggravate cerebral edema, and interfere with intracellular signaling in cerebral tissues (Hansson, 2005). Recently, the β-amyloid (Aβ) protein has been identified as an important marker of SBI. The Aβ protein is also known to be involved in the cerebral plaque formations that contribute to senility in Alzheimer disease patients (Goedert and Spillantini, 2006), and has a strong tendency for aggregation and high neurotoxicity that can induce SBI following TBI (Loane et al., 2009). Aβ protein aggregates are extremely difficult to dissolve in nerve cells, particularly in the presence of β-secretase (BACE) that acts as the key rate-limiting enzyme in Aβ protein formation by hydrolysis of the β-amyloid protein precursor (APP) at the amino terminus (Uryu et al., 2007; Mannix et al., 2011). When Aβ aggregates outside of nerve cells, it can also promote abnormalities in neuronal cytoskeleton, resulting in cellular damage (Loane et al., 2009). In addition, Aβ may also be responsible for abnormal and potentially adverse metabolic activities, such as low glucose levels, elevated neuronal excitability, oxidative stress in various tissues, intracellular calcium imbalance, and promotion of inflammatory response processes (Lindholm et al., 2006). Recently, it has been reported that MIH treatment effectively reduced upregulation of Aβ, BACE, and the β-amyloid protein precursor (APP) after TBI, limiting adverse effects associated with SBI. (Cheng, et al., 2013). Thus, it has been postulated that hypothermia treatment may enhance neuroprotective functions by inhibiting neurotoxicity through the suppression of Aβ and BACE expression. (Cheng, et al., 2013).

Separately, other researchers have discovered that a brain waste-draining system dubbed the "glymphatic system" is ten times more active during sleep than while awake. (Xie, et al., 2013). This glymphatic system removes β-amyloid, which is believed to accumulate into the plaques that contribute to Alzheimer's disease and dementia. The system in purported to work by causing cerebrospinal fluid (CSF) to flow through the spaces between neurons, flushing proteins and other neural waste into the circulatory system and away. (Xie, et al., 2013). It is postulated that the flushing of the CSF occurs during periods of deep sleep, when the brain region may be less active and cooler, opening up channels that allow the CSF to flow. Cooling of the brain region with the transnasal cooling method described herein can also facilitate cooling and CSF flow to help flush proteins, β-amyloid and other waste products away.

Thus, the invention provides a method for inhibiting, reducing the expression, up-regulation, and/or accumulation of β-amyloid, BACE, and/or APP, particularly, although not exclusively, following traumatic brain injury. As the accumulation of β-amyloid is also associated with senile dementia and Alzheimer's, the invention also provides a method for delaying or preventing the onset of senile dementia, and delaying or preventing the onset of Alzheimer's. According to each of these methods, dry air is blown across a patient's internal mucous membranes, especially those in the nasal turbinates, using the devices described herein.

In cases where there is not a need to cool the body or remove excess heat or fluid, the invention provides a method for the extraction of fluid and energy resulting increased metabolism (the body's natural response to energy loss), thereby promoting weight loss.

According to another embodiment, the invention may be used to prevent esophageal burn-through during catheter ablation treatment for atrial fibrillation. Catheter ablation treatment for atrial fibrillation can sometimes result in catastrophic burn-through of the esophageal wall. See, e.g., http://circ.ahajournals.org/content/113/13/e666.full ("Rarely, ablation may damage the esophagus, which is located behind the left atrium, leading to fatal bleeding or stroke several days after the procedure."). Researchers are looking for ways to monitor and reduce the temperature of the esophageal wall in order to prevent burn-through. The present invention may be readily adapted to introduce dry air to the esophagus, causing evaporative cooling of the esophageal mucous membrane and surrounding tissues, thus reducing the risk of esophageal burn through during catheter ablation treatment for atrial fibrillation.

According to an esophageal burn-through prevention embodiment, a simple disposable NG tube with a small balloon at the distal end may be provided. According to this embodiment, the tube may be placed in the patient's esophagus just above the stomach and is connected to a source of dry air. The balloon creates a seal that keeps the air from going into the stomach. The dry air comes out the distal end of the tube (through holes in the distal end of the tube), up through the esophagus and out the nose and mouth. The size of the air holes can be designed to achieve a desired pressure in the NG tube, which is also sufficient to inflate the balloon seal. The mucus glands in the esophagus moisturize the air, removing energy from the body. According to a further embodiment of this invention, one or more thermistors may be embedded in the disposable tube that could be used to monitor temperature in the esophagus (near the catheter ablation treatment area.)

Figure 5:
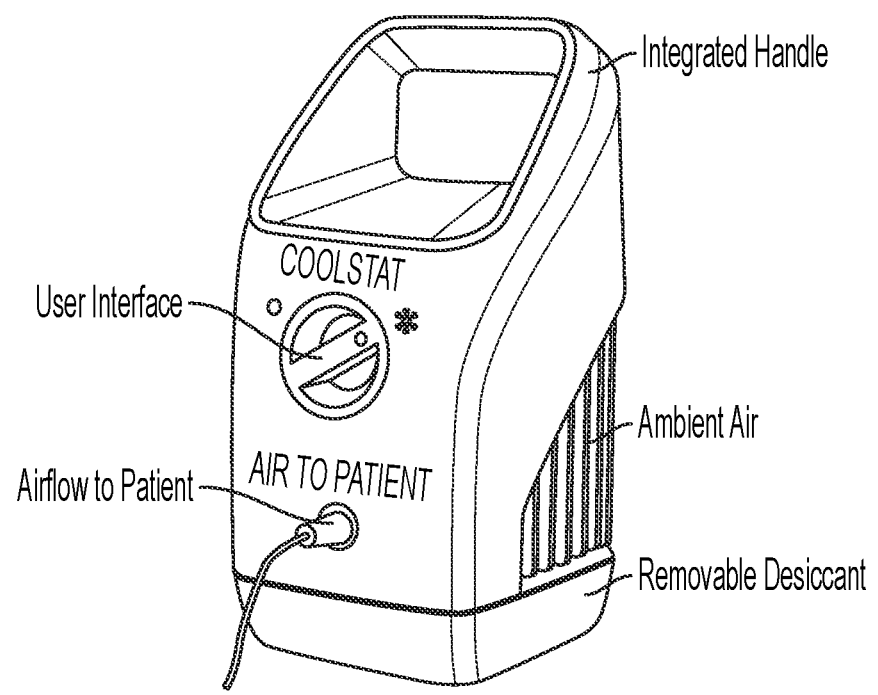
FIG. 5 is a representation of a device according to one embodiment of the invention.

FIG. 5 shows a representation of a portable device according to the invention that may be used to carry out the new methods according to the invention.

According to a preferred embodiment, a device according to the invention will have the following elements: a fan to move the air, a single-use replaceable desiccant cartridge to remove moisture from the air flow, various flow, pressure, humidity and temperature sensors, and one or more batteries along with standard connections for wall power (110V). In addition, the device interface may be configured to allow an operator to select the dosing level (based on patient age and/or size), which will set the air flow rate. The device may also be provided with a pressure limit for each dosing level to limit the pressure that could be delivered to the patient as a safety feature. It is recognized that the removal of moisture from the air (via the desiccant cartridge) will generate heat as a byproduct of extracting the moisture from the air stream. This could cause the desiccated air to become excessively warm (e.g., >40 C). As such, the device embodiment will have one or more heat sinks/heat exchangers to remove this heat and dissipate it to the environment. The heat sink may be a passive, finned component, typically used to remove excess heat from inside electronic enclosures. The heat sink may be a feature incorporated into the air tubing used to carry the dry air from the device to the patient, such that the heat in the air is dissipated to the environment along the length of the air tubing, as the air flows to the patient. The heat sink may have a fan to blow air across the finned components (internal and/or external to the device) to improve the heat removal, and possibly might also include the use of other active means to increase heat removal such as using peltier elements. The peltier elements (or other heating techniques) might also be used to heat the air being supplied to the patient in cold weather environments when the incoming air the patients might be excessively cold.

Figure 6:
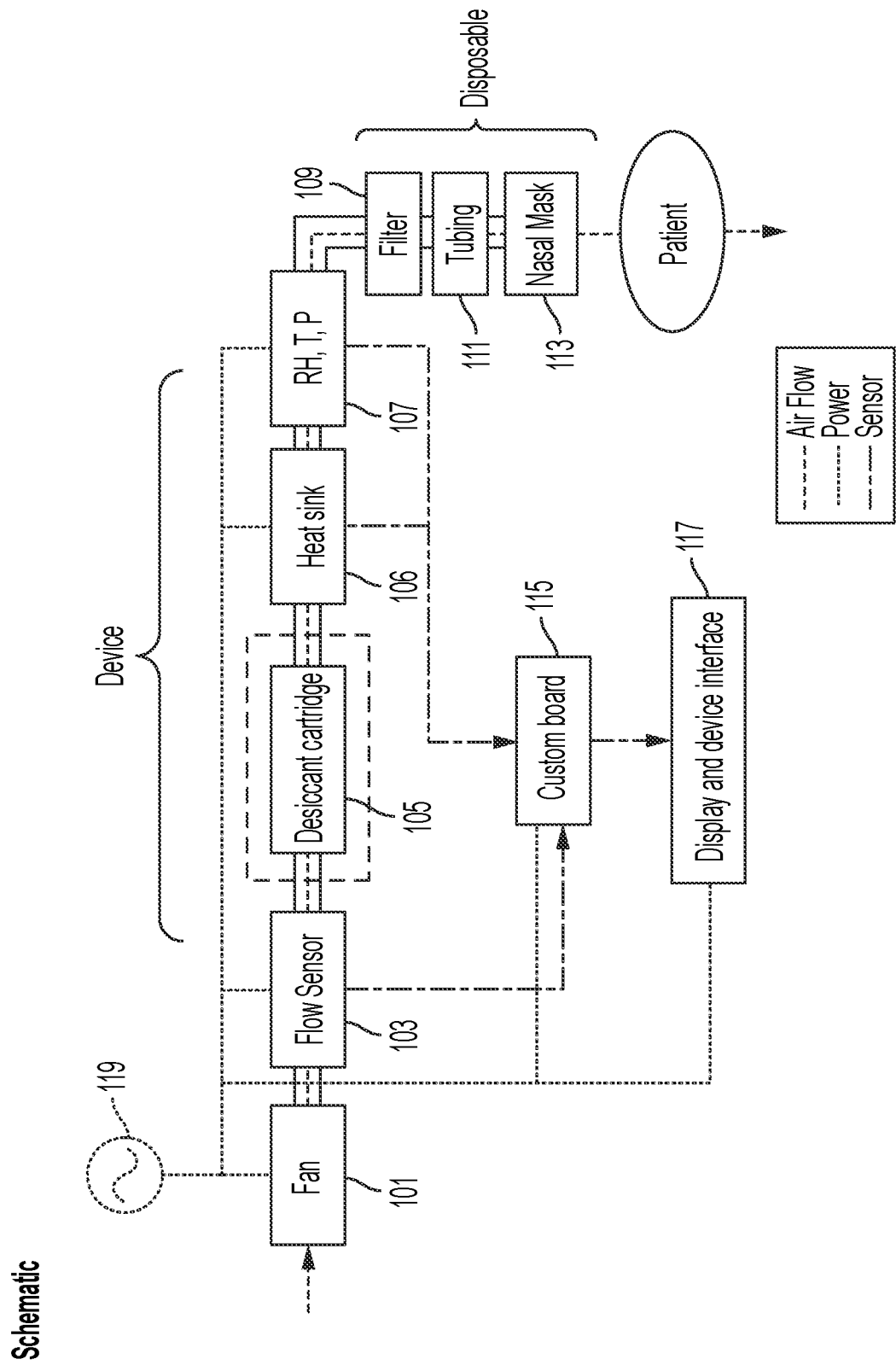
FIG. 6 is a schematic of an apparatus for delivering large volumes of dry gas, not including a coolant, to the bodily fluid-containing space which gas is expelled or withdrawn from the space after it has exchanged energy with the body fluid containing space.

FIG. 6 shows a schematic of a device according to one embodiment of the invention which air flow is generated by fan 101, and in which the air flow passes through or by air flow sensor 103, desiccant cartridge 105, heat sink 106, humidity, pressure and temperature sensor(s) 107. According to the embodiment shown in FIG. 6, after the air has left the device, it may pass through disposable filter 109, tubing 111, and/or nasal mask 113 for delivery to the patient. Flow sensor, heat sink, and/or humidity, temperature and pressure sensors may be in communication with processor or custom board 115, which in turn may be in communication with display and device interface 117. Power source 119, may be A/C or D/C, and may be supplied by on-board battery or external power source, and/or both. The desiccant cartridge 105 may be disposable and replaceable.

Figure 7:
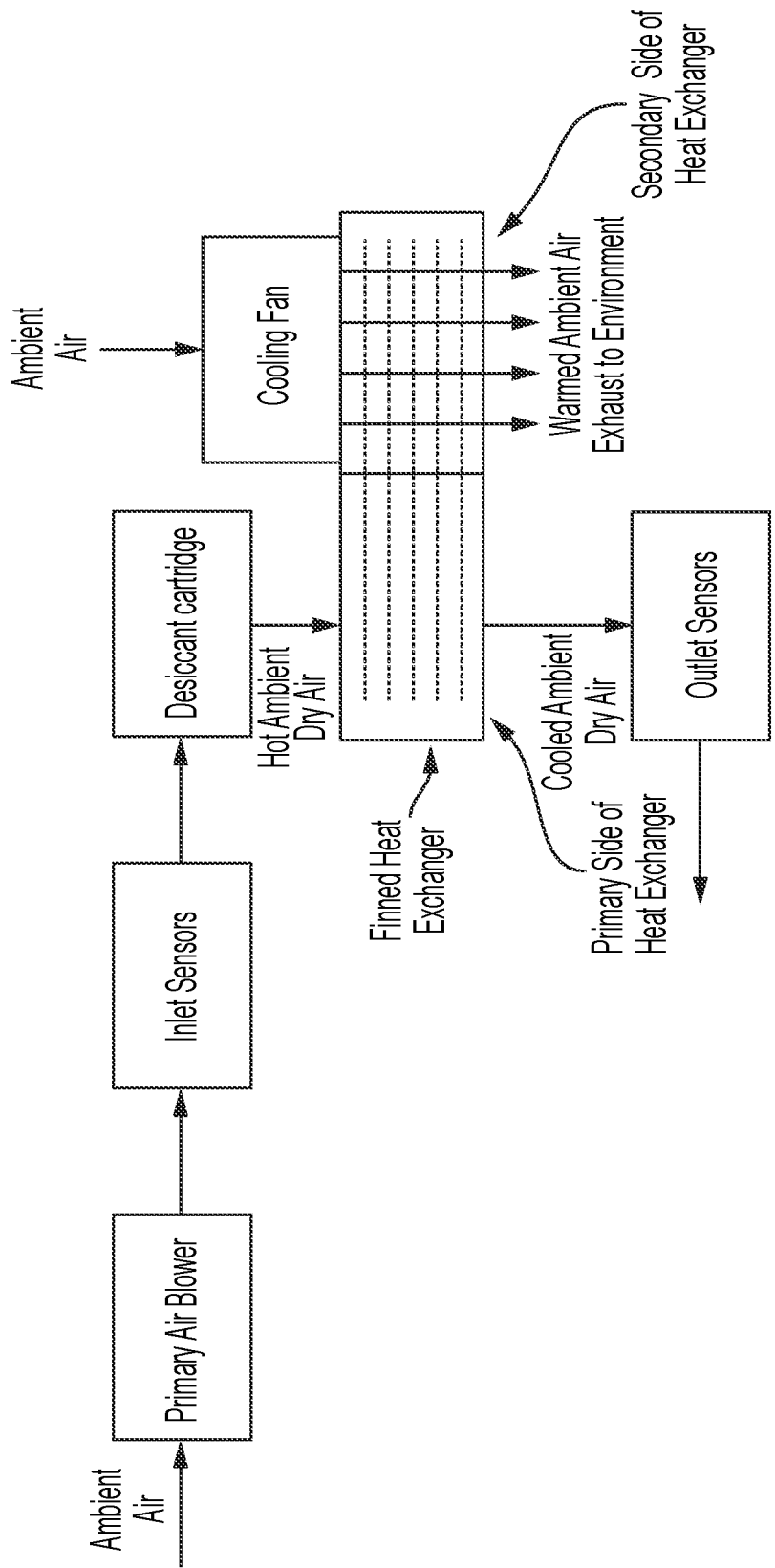
FIG. 7 is a schematic of another embodiment of delivering large volumes of dry gas, not including a coolant, to the bodily fluid-containing space which gas is expelled or withdrawn from the space after it has exchanged energy with the body fluid containing space.

FIG. 7 shows an embodiment of the invention having a two-sided heat sink/heat exchanger. As the desiccant material removes water from the airstream, heat is released, warming the air. Because the air can be heated to temperatures in excess of 50° C. without intervention, a cooling module may placed downstream of the desiccant cartridge to remove the excess heat before the air exits the device and reaches the patient. Therefore, according to the embodiment shown in FIG. 7, a two-sided heatsink is used, with one side placed along the flow path of the hot air exiting the desiccant cartridge (the "primary" side of the heatsink). A cooling fan blows ambient air across the other side of the heatsink (the "secondary" side). A barrier between the sides prevents any air from physically mixing or communicating between the two, but allows the communication of heat across the barrier. Due to the difference in temperature between the two airstreams, the heatsink conducts heat away from the air on the primary side and warms the ambient air provided by the cooling fan on the secondary side. The dry air thus exits the heat exchanger on the primary side having been significantly cooled and ready to be administered to patients or provided as a source of cooling air inside a protective containment suit or other applications. The now-warmed air exiting the secondary side is released back into the environment. This same effect could be obtained via other methods of cooling in place of the secondary side of the heatsink, such as a thermoelectric cooler (Peltier cooler), chemical reaction, or refrigeration cycle.

Figure 8:
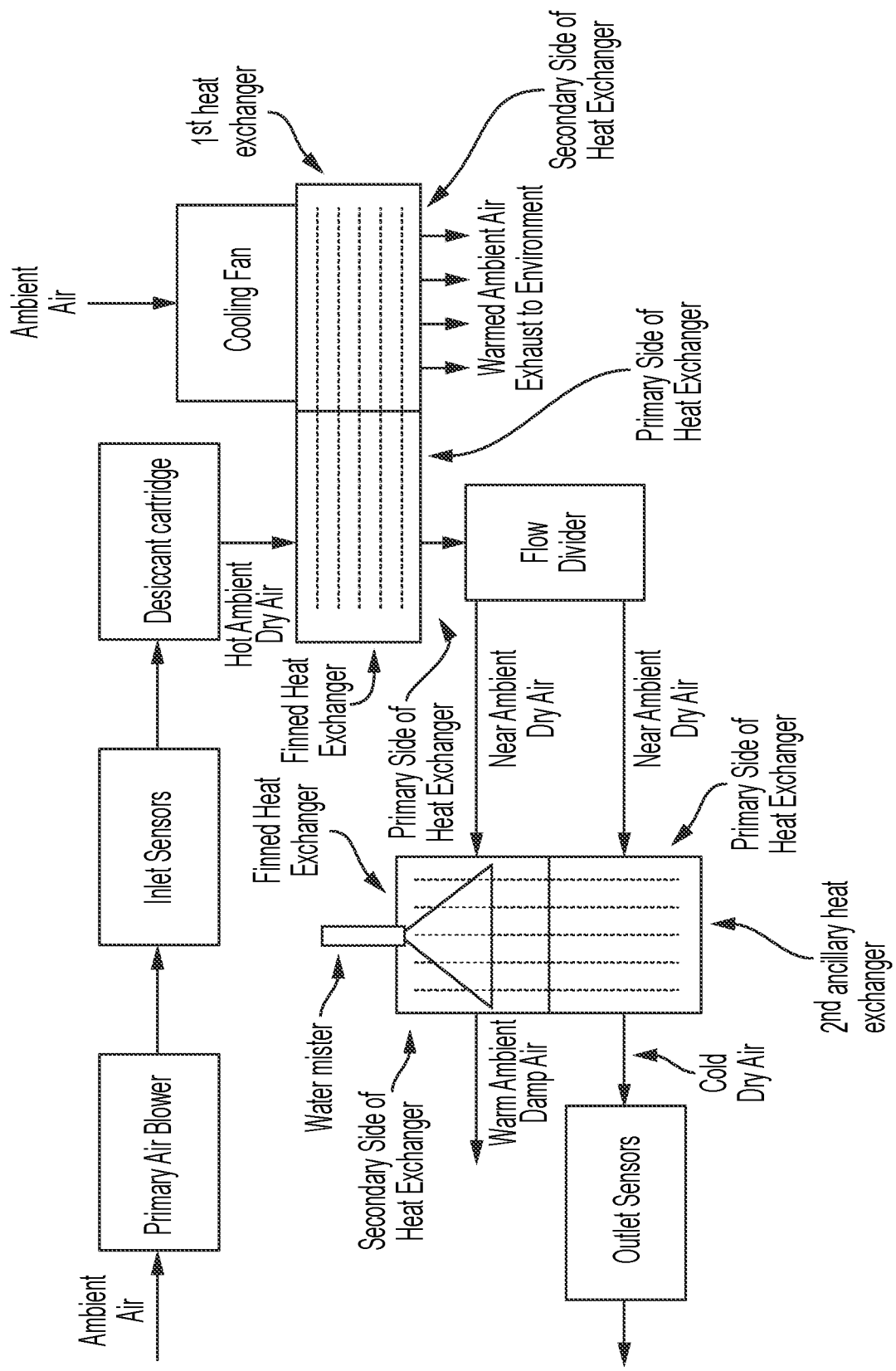
FIG. 8 is a schematic of another embodiment of delivering large volumes of dry gas, not including a coolant, to the bodily fluid-containing space which gas is expelled or withdrawn from the space after it has exchanged energy with the body fluid containing space.
Figure 9:
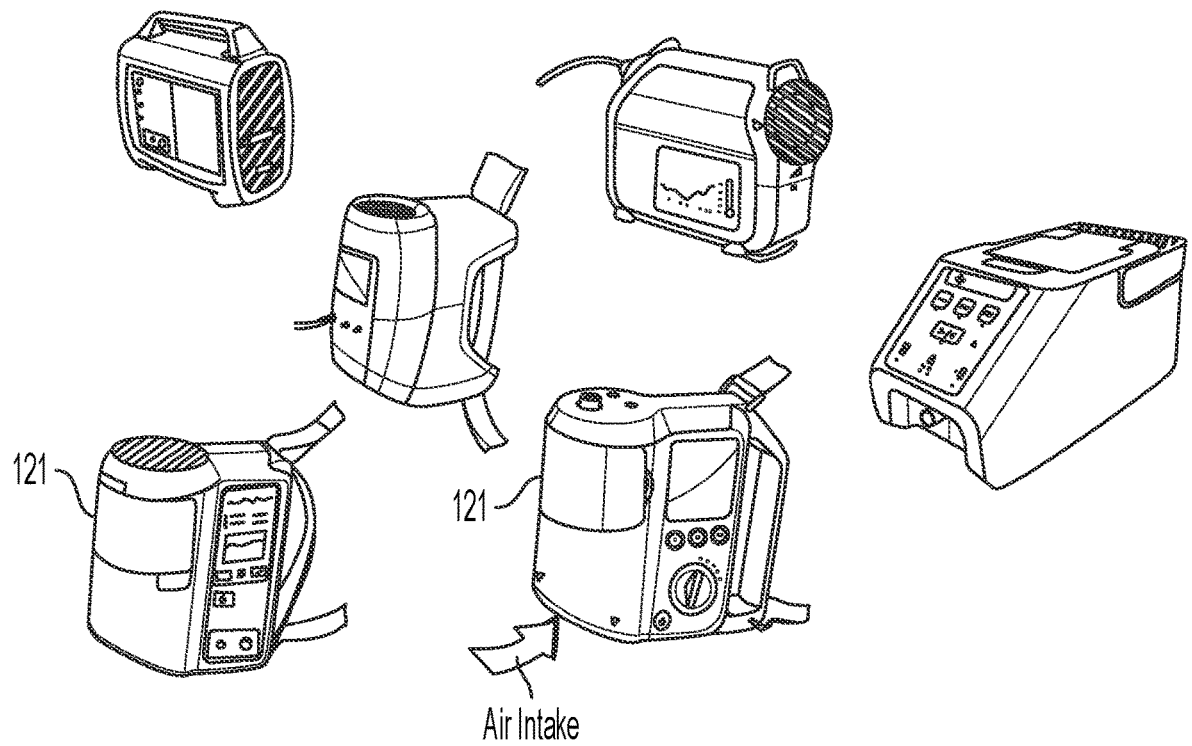
FIG. 9 is a representation of six different embodiments of a portable apparatus according to the invention.

FIG. 8 shows a further embodiment in which a second, ancillary heat exchanger can be placed downstream of the first exchanger, which can be used to further cool the dry air exiting the primary side of the 1st heat exchanger. A flow divider can be used to divert a portion of the dry air exiting the first heat exchanger (on the primary side) to the 2nd ancillary heat exchanger. Note that the air exiting the first heat exchanger (on the primary side) will be cooler than the inlet temperature (on the primary side) and will asymptotically approach ambient temperature, but will be no cooler than the ambient temperature (since the cooling source in the first heat exchanger is from ambient air). As a means to cool this air further, a mister can be used periodically to spray a thin film of water onto exposed surfaces of the secondary side of the 2nd ancillary heat exchanger. As the dry air passes through the secondary side of the 2nd heat exchanger, water is evaporated from these surfaces, which is then carried into the air stream. This state change requires energy, which will be drawn from the wetted base material of this heat exchanger, causing the secondary side of this heat exchanger to cool. As it cools, the heatsink will induce a transfer of energy/heat from the dry air passing through the primary side of the 2nd heat exchanger, cooling that air to an even greater degree before it exits the device. This will create a source of air that is both dry and at a lower temperature than the starting ambient temperature FIG. 9 shows various portable embodiments of the invention, each of which may include carrying handles and/or straps, display interfaces, air intakes, and control interfaces/knobs. The bottom two embodiments shown in FIG. 9 include panels 121, through which a removable desiccant cartridge may be removed and replaced.

Figure 10:
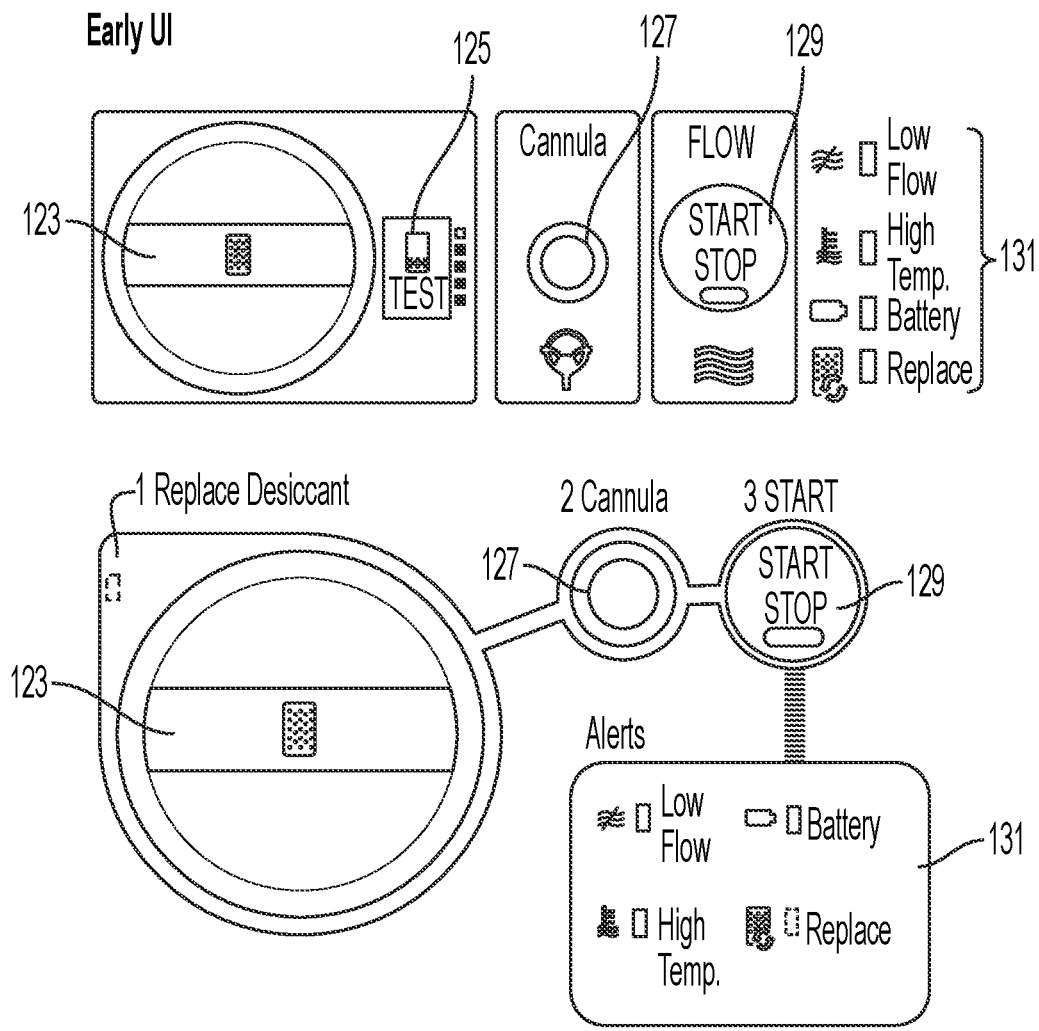
FIG. 10 shows a representation of two embodiments of a user interface for an apparatus according to an embodiment of the invention.
Figure 11:
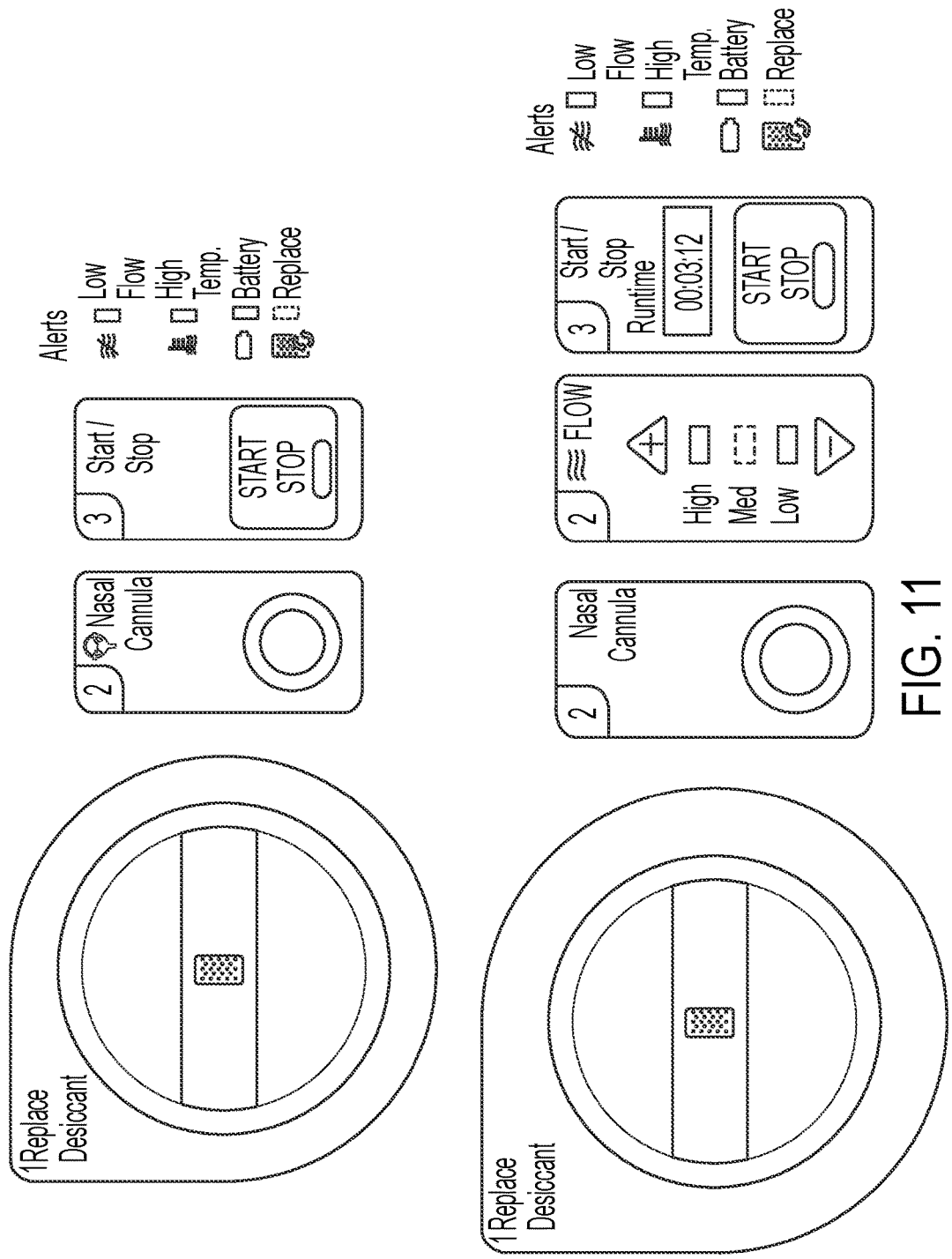
FIG. 11 shows a representation of two further embodiments of a user interface for an apparatus according to an embodiment of the invention.

FIGS. 10 and 11 show various interfaces for the control and monitoring of devices according to different embodiments of the invention, as well as cannula/tubing attachment interfaces. The interface shown at the top of FIG. 10 shows twist-off cap 123 for accessing a removable desiccant cartridge, a desiccant cartridge test button 125, cannula port 127 for removably connecting the tubing which directs the air flow to the patient, start button 129, which the user may use to turn on and off the air flow, and indicator lights 131, which are used to indicate low or blocked air flow, high temperature/overheating of the device, battery strength, and desiccant cartridge replacement. The interface embodiment shown at the bottom of FIG. 10 shows the same features in a slightly different configuration. Various interface features may be visually linked by printing or other designation on the device indicating to the user the order in which to interact with each interface. The embodiment shown at the bottom of FIG. 10, for example indicates that the first step is to load the desiccant cartridge, that the second step is to connect the delivery cannula to the device and patient, and that the third step is to press the Start/Stop button to start air flow to the patient.

FIG. 11 interface embodiments including printed numbers to indicate to the user the order in which to interact with each interface. The interface embodiment shown at the bottom of FIG. 11 shows the interface for a device which gives the user the ability to adjust the air flow rate between high, medium and low levels, and also indicates the run time of the device.

Figure 12:
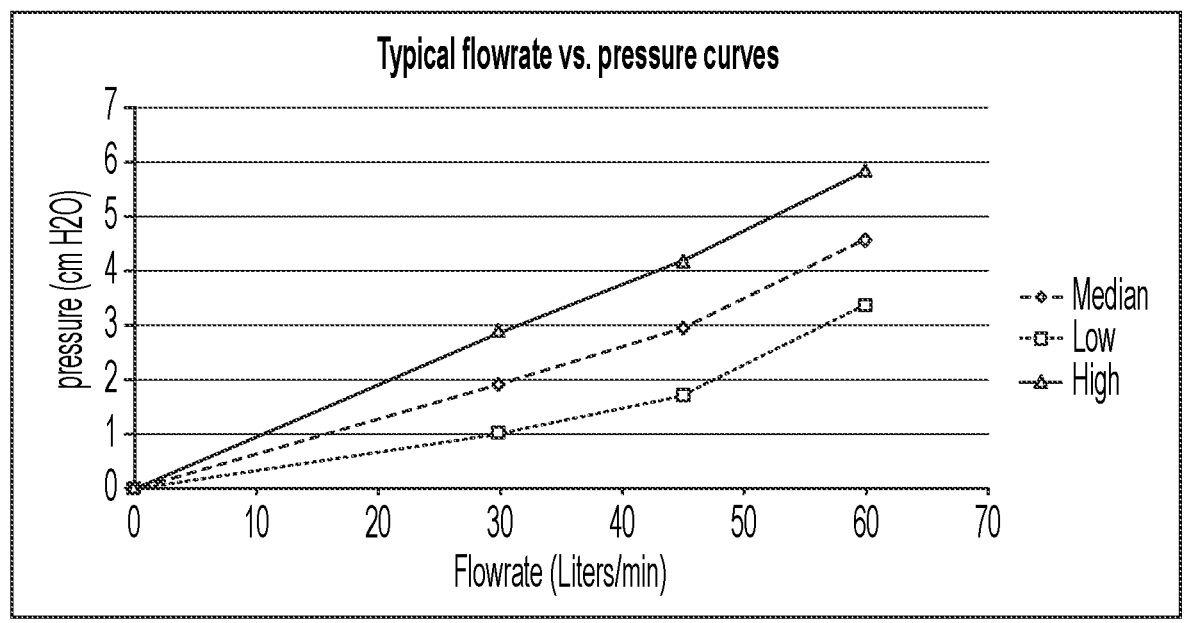
FIG. 12 is a chart showing typical device flowrate vs. pressure curves, where the pressure drop is measured across the nasal turbinates of the patient.

FIG. 12 is a chart showing flow rate and pressure, typical for air flow across the nasal turbinates of a human. According to a preferred embodiment, the device may measure delivered airflow and pressure, and compare it to data representing normal, high, and/or low flow rate and/or pressure, of the type shown in FIG. 12. If measured conditions are outside of a specified range (high or low), the device may be configured to alarm, either sound, or light, or both, telling the operator that there may be an occlusion (e.g., a blockage in the throat or nasal passages) or a leak.

Figure 13:
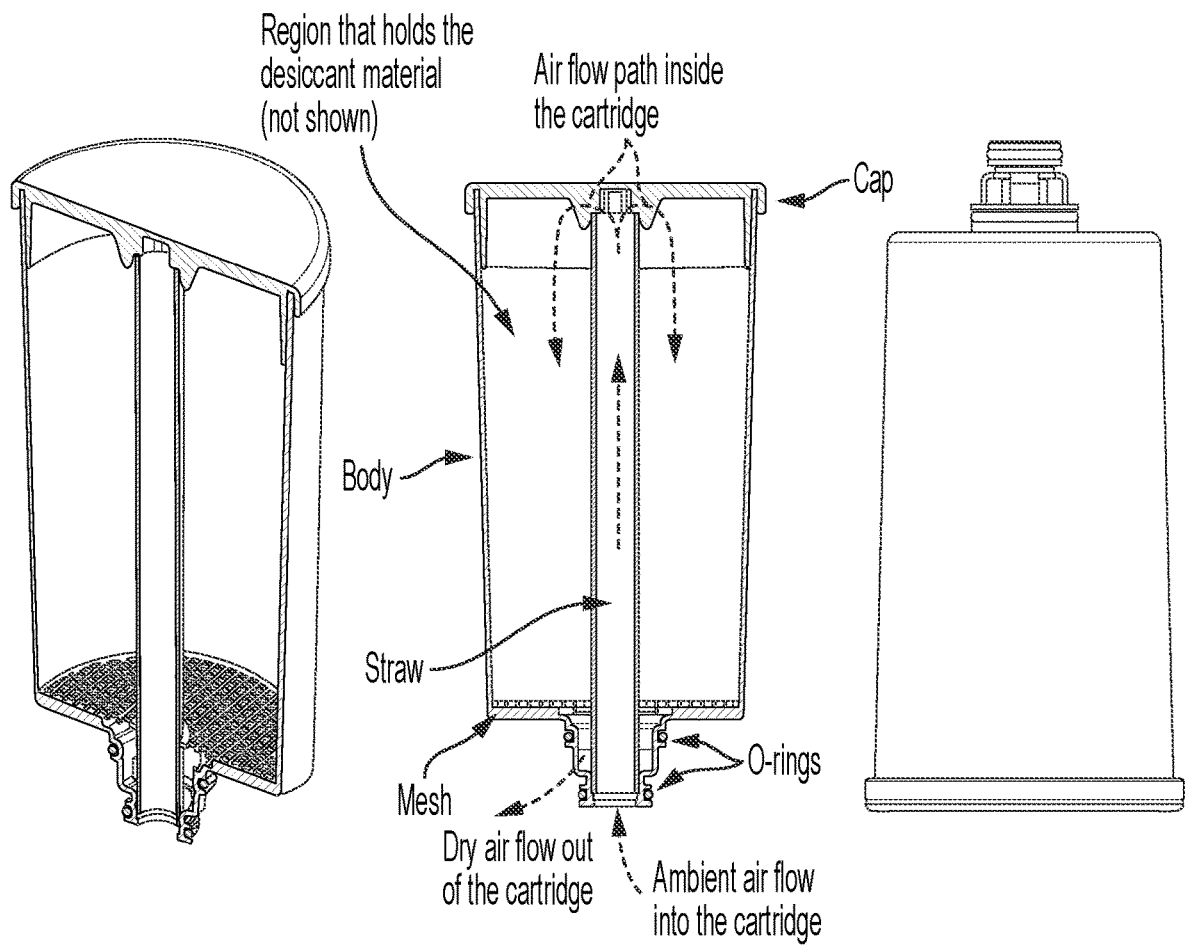
FIG. 13 shows an embodiment of a desiccant cartridge that may be used to hold the desiccant material in the device.

FIG. 13 shows an embodiment of a disposable cartridge which may be composed of three primary components: a main body, a cap, and a central "straw". There may also be a mesh to contain the desiccant material (so it cannot leak out of the cartridge) and a pair of O-rings to create a seal between the disposable cartridge and the device. To assemble the cartridge, the top cap is removed and the straw is placed into the body and held in place by a friction fit. The mesh may be placed around the straw and pushed down so that it makes contact with the bottom of the cartridge body (as shown in FIG. 13). Although not shown, ribs may be provided to act as standoffs, holding the mesh slightly above the bottom of the cartridge. In addition to adding strength to the body, the ribs may also offset the mesh above the body surface, allowing for greater airflow. The desiccant material is then poured into the body and the cap is snapped on or otherwise attached. The O-rings are preferably configured to mate with a pair of female features in the device, creating radial seals that separate the inlet from the outlets.

In various embodiments, the device may further include additional features that allow for the introduced fluid to be exhausted from the bodily fluid-containing cavity; see U.S. patent application Ser. No. 13/579,370 paragraph [0047], which is incorporated herein by reference.

Any configuration of fluid delivery ports, alone or in combination with return ports is envisioned to achieve desired gas flow to result in fluid elimination, anatomic or systemic cooling, energy removal, metabolic rate adjustment and/or weight loss, see U.S. patent application Ser. No. 13/579,370, paragraph [0055], which is incorporated herein by reference.

The device may include a number of additional features to assist in regulating gas flow and pressure to achieve fluid elimination, anatomic or systemic cooling, energy removal, metabolic rate adjustment and/or weight loss. The device may further include a temperature sensor and/or pressure sensor for dynamic feedback and control of the gas temperature, pressure, and gas flow; see U.S. patent application Ser. No. 13/579,370, paragraph [0057], which is incorporated herein by reference.

The duration of treatment will vary depending on the desired level of fluid elimination, anatomic or systemic cooling, energy removal, metabolic rate adjustment and/or weight loss.

It has been established that is related to the flow rate and dryness of the gas, wherein an increase in flow rate and decrease in dryness increases the rate. As such, an appropriate technique for determining the desired duration to provide treatment is determined by monitoring.

Where the desired result is fluid elimination, the duration of treatment may be determined by monitoring flow rate, temperature and change in humidity level (from inlet to exhaust). Where the desired result is energy removal/metabolic rate adjustment/weight loss, the duration of treatment may be determined a similar approach. In the case of metabolic rate adjustment to promote weight loss, the invention may be used overnight over a longer period of time. The gas flow rate may be set at a lower flow rate, e.g., between 20 and 40 L/min, to improve tolerability. The therapy can also be intermittently paused to allow the mucus-containing space or surface to recover, if needed.

In various embodiments, the gas is delivered to a bodily fluid-containing space or surface. Such spaces and surfaces may include, but are not limited to the lungs, trachea, oral cavity, nasopharynx, nostrils, gastro-intestinal system, stomach, peritoneal cavity, skin and urinary bladder. In various embodiments, the body fluid-containing space or surface is a mucus-containing space or surface, for example, any space or surface that secretes or includes mucus, such as mucosal membranes or cells.

According to a further embodiment of the invention, the dry gas/air may be provided to the nasal turbinates in pulses, either in the same nostril, or alternating between nostrils. The nasal passages have developed such that they are highly evolved to support normal breathing patterns, even during periods of high flow demand, such as when someone is running outside in dry, cold air. In the case of the runner, he/she can inhale air through the nose at high flow rates for short periods of time, on the order of 30 LPM (and higher) for a duration of up to 2 to 3 seconds, before exhaling over the same period of time. The nasal passages are able to accommodate this type of pulsing flow of air with no or very little discomfort.

Accordingly, the present invention includes embodiments that induce transnasal cooling that pulses the air flow through the nasal turbinates. According to this embodiment, dry air is first directed only into nostril 'A' at relatively high flows, up to 60 to 80 LPM. The dry air flows into nostril 'A' and out of nostril 'B' and/or the mouth. This flow is maintained only for several seconds at which point the flow direction is switched. The flow of air is then directed into nostril 'B' and flows out of nostril 'A' and/or the mouth. Similarly, the air flow into nostril 'B' is maintained only for several seconds (2-3 seconds, 3-5 seconds, 2-5 seconds, 5-7 seconds, 5-10 seconds, 7-20 seconds, or 2-10 seconds) before switching back to nostril 'A'. The cycling of air back and forth between each nostril continues over the entire transnasal cooling period, which can last 60 minutes or more. This type of pulsed flow is similar to conditions that each individual nasal passage sees in normal use. By implementing this type of flow pattern, the discomfort which occurs when the air flow is continuous in only one direction is relieved. Preliminary testing has shown that there is less discomfort with this type of pulsed flow model.

According to this embodiment of the invention, air supply device may provide air to the nostrils via two tubes or lumen, one for each nostril. The device may be configured to alternate the flow of air through the tubes/lumen, first through one tube/lumen, then through the other, according to the period/frequency set by the device or the user. According to an alternative configuration, the device may be configured to provide air through one tube/lumen and suction through the other, with the flow of air and the amount of suction configured to provide a net pressure of near zero, and according to the period/frequency setting, the suction and blowing functions are reversed for each tube/lumen.

Unless otherwise set forth otherwise, the embodiments described above are generally directed towards creating a positive pressure source to blow dry air into the nose and nasal turbinates, which induces the evaporative phenomenon. According to these embodiments, air enters through the nose and exits the mouth, and about 20 to 30 cm of water pressure is generated in order to create the preferred air flow according to most preferred embodiments, but other embodiments use pressures up to 40 cm, 50 cm and 60 cm of water pressure.

However, testing using these embodiments has shown that as pressure is increased, the fine vasculature in the turbinates is compressed, causing a reduction in blood flow and water supply, which in turn reduces the vascular supply of heat which is needed to support evaporative cooling. Separately, evaporation (from any surface) decreases as air pressure increases.

Accordingly, the present invention also includes the creation of air flow over the nasal turbinates through the use of a vacuum or other suction. According to these embodiments, two air tubes would be provided, one connected to each nostril. A negative pressure source (e.g., a fan) or vacuum source is connected on one side to pull dry air into the other side. The dry air enters a first nostril, travels across one side of the turbinates, and goes out the other nostril (the side with the negative pressure source). This negative pressure/vacuum source also causes vasodilation, which improves the vascular supply of heat and thus improves the evaporative model, even beyond normal respiratory conditions. This embodiment of the invention has an additional benefit in that the user need not be concerned about venting from the mouth; that is, the mouth need not be kept open. This embodiment is also unaffected by possible occlusions in the upper airway, which could block air flow according to other embodiments. According to a preferred embodiment, the fan or vacuum causes air to be drawn through a desiccant cartridge prior to entering the first nostril. According to another embodiment a blower may be provided at the inlet side so that the net gage pressure across the turbinates is very low or zero, with the positive pressure fan/blower and the negative pressure vacuum source balancing one-another out. According to embodiments where a vacuum source is provided at one nostril, a seal may be placed between the inlet nostril and the inlet tube to prevent or inhibit the entry of ambient (non-desiccated) air from entering the inlet nostril The heat/energy/fluid removal model according to the invention can also be used in series or parallel with two or more mucus membranes throughout the body. The inventors have discovered that different mucous membranes may be used in an additive fashion to increase the amount of energy removal, cooling, fluid removal, and other effects. In particular, the inventors have observed in animal studies that the simultaneous flow of dry air/gas across the mucous membranes in nasal turbinates and in the esophagus resulted in increased cooling. Accordingly, this invention includes methods and devices which introduce dry non-coolant gas/air to the nasal turbinates and which simultaneously also introduce dry non-coolant gas/air to mucous membranes in the esophagus. The method can be carried out by using two devices, one which is used to supply dry non-coolant gas/air to the nasal turbinates, which gas/air, upon being conditioned/humidified by the mucous membranes in the nasal turbinates, exits the mouth, and a second device which is used to supply dry non-coolant gas/air to the esophagus, which gas/air, upon being conditioned/humidified by the mucous membranes in the esophagus, also exits the nose and/or mouth. Additionally, the invention includes a single device which is configured to supply non-coolant gas/air to the nasal turbinates via a nasal turbinate delivery tube and non-coolant gas/air to the esophagus via a separate esophagus delivery tube.

This additive effect may also be used in various combinations of other membranes/organs, including two or more of any of the following: nostrils, esophagus, lungs, trachea, oral cavity, nasopharynx, gastro-intestinal system, stomach, and urogenital mucus-containing spaces.

Although the invention has been described with reference to the above example, it will be understood that modifications and variations are encompassed within the spirit and scope of the invention. Accordingly, the invention is limited only by the following claims.

What is claimed is:

1. A portable device for inducing evaporation of a fluid from a bodily fluid-containing space in a mammal, the device comprising, in an integrated unit:
   an air inlet,
   an inlet sensor configured to measure air temperature or pressure or both;
   a desiccant chamber configured to receive a removable and replaceable desiccant element;
   an air outlet configured to connect to an air delivery tube;
   a blower configured to draw a first flow of ambient air into the device via the air inlet and force said first flow of ambient air in a first flowpath across said desiccant chamber and out said air outlet;
   a heat exchanger located in said first flowpath downstream of said desiccant chamber, said heat exchanger comprising a fan configured to draw a second flow of ambient air into a heat exchanger cooling air inlet to accept heat from said first flow of ambient air without contacting said first flow of ambient air and exit said device via a heat exchanger cooling air outlet;
   an atomizer or nebulizer configured to administer water to said bodily-fluid containing space, and
   an outlet sensor configured to measure air temperature or pressure or both;
   said air inlet, blower, desiccant chamber, and air outlet arranged in series along an air flow path.

2. A portable device according to claim 1, further including user control configured to allow a user to deliver dry air that is at ambient temperature, warmer than ambient temperature, or cooler than ambient temperature.

3. A portable device according to claim 1, further comprising a negative pressure source and an attachment site for attaching a tube configured to draw warmed and humidified gas from a bodily fluid containing space of a mammal.

* * * * *